(12) United States Patent  
Kim

(10) Patent No.: US 10,874,867 B2  
(45) Date of Patent: Dec. 29, 2020

(54) DEFIBRILLATOR COMPRISING LADDER BRIDGE CIRCUIT

(71) Applicant: RADIAN CORPORATION, Seoul (KR)

(72) Inventor: Beom Ki Kim, Seoul (KR)

(73) Assignee: RADIAN CORPORATION, Seoul (KR)

(*) Notice: Subject to any disclaimer, the term of this patent is extended or adjusted under 35 U.S.C. 154(b) by 175 days.

(21) Appl. No.: 15/904,619

(22) Filed: Feb. 26, 2018

(65) Prior Publication Data

US 2018/0177999 A1     Jun. 28, 2018

Related U.S. Application Data

(63) Continuation of application No. PCT/KR2016/009103, filed on Aug. 18, 2016.

(30) Foreign Application Priority Data

Aug. 27, 2015   (KR) .................. 10-2015-0120696

(51) Int. Cl.
| | |
|---|---|
| *A61N 1/05* | (2006.01) |
| *A61N 1/39* | (2006.01) |
| *H03K 17/567* | (2006.01) |
| *H03K 17/73* | (2006.01) |
| *H03K 17/687* | (2006.01) |

(52) U.S. Cl.
CPC ............. *A61N 1/3904* (2017.08); *A61N 1/05* (2013.01); *A61N 1/3912* (2013.01); *A61N 1/3931* (2013.01); *H03K 17/567* (2013.01); *H03K 17/6871* (2013.01); *H03K 17/73* (2013.01); *A61N 1/3906* (2013.01); *A61N 1/3975* (2013.01)

(58) Field of Classification Search
USPC ............................................................. 607/5
See application file for complete search history.

(56) References Cited

U.S. PATENT DOCUMENTS

2005/0187583 A1* 8/2005 Garrett ................ A61N 1/39  
607/5

FOREIGN PATENT DOCUMENTS

| EP | 2 229 978 A1 | 9/2010 |
| JP | 4931995 B2 | 5/2012 |
| KR | 10-2007-0114116 A | 11/2007 |
| KR | 10-0948671 B1 | 3/2010 |
| KR | 10-1049172 B1 | 7/2011 |

OTHER PUBLICATIONS

International Search Report; issued in PCT/KR2016/009103; dated Dec. 1, 2016.

* cited by examiner

*Primary Examiner* — Nicole F Lavert  
*Assistant Examiner* — Nicole F Johnson  
(74) *Attorney, Agent, or Firm* — Studebaker & Brackett PC

(57) ABSTRACT

A defibrillator disclosed in the present application including at least: a high voltage capacitor charged through a battery power source; a ladder bridge circuit connected to one end of the high voltage capacitor; a control unit for controlling an on/off operation of switching elements constituting the ladder bridge circuit, wherein the ladder bridge circuit comprises: a first circuit unit and a second circuit unit, one ends of which are connected to one end of the high voltage capacitor and which are connected in parallel to each other; and a third circuit unit connected in series to the other ends of the first circuit unit and the second circuit unit.

2 Claims, 5 Drawing Sheets

DEFIBRILLATOR COMPRISING LADDER BRIDGE CIRCUIT

CROSS-REFERENCE TO RELATED APPLICATIONS

The present application is a continuation of International Patent Application No. PCT/KR2016/009103, filed on Aug. 18, 2016, which is based upon and claims the benefit of priority to Korean Patent Application No. 10-2015-0120696, filed on Aug. 27, 2015. The disclosures of the above-listed applications are hereby incorporated by reference herein in their entirety.

TECHNICAL FIELD

The present invention relates to a defibrillator including a ladder bridge circuit, and more particularly, to a defibrillator in which a ladder bridge circuit having an overvoltage charging or electric shock protection function more improved than that of an H bridge circuit is configured as an output circuit.

BACKGROUND ART

Generally, H bridge circuits are electronic circuits that enable a voltage to be applied across a load in a certain direction. The circuits are often used in many applications in which robots, defibrillators, and direct current (DC) motors can operate in forward and reverse directions.

The H bridge circuits are mostly used as DC-to-alternating current (AC) converters, AC-to-AC converters, DC-to-DC push-full converters, motor controllers, or many other types of power electronic circuits.

As the electronic circuits become more advanced and complicated, circuits that can safely handle higher voltages than conventional H-bridge circuits are required.

Technical Problem

The present invention is directed to providing a defibrillator including a ladder bridge circuit which is more stable than an H bridge circuit at a high voltage.

Technical Solution

One aspect of the present invention provides a defibrillator including a high voltage capacitor charged through a battery power source, a ladder bridge circuit connected to one end of the high voltage capacitor, and a control unit configured to control on/off states of switching elements constituting the ladder bridge circuit, wherein the ladder bridge circuit includes a first circuit unit and a second circuit unit having one ends connected to one end of the high voltage capacitor and connected in parallel, and a third circuit unit connected in series to the other ends of the first circuit unit and the second circuit unit, the first circuit unit includes a first switching element having one end connected to the high voltage capacitor and a second switching element connected in series to the other end of the first switching element, the second circuit unit includes a third switching element having one end connected to the high voltage capacitor and a fourth switching element connected in series to the other end of the third switching element, and the third circuit unit includes a fifth switching element and a sixth switching element connected in parallel and having one ends connected to the other ends of the first circuit unit and the second circuit unit.

The ladder bridge circuit may further include a first load connected between the second switching element and the fifth switching element and a second load connected between the fourth switching element and the sixth switching element, and the first load and the second load may be electrically connected when a load is connected thereto.

The ladder bridge circuit may further include a fourth circuit unit including a seventh switching element connected in series to the fifth switching element and an eighth switching element connected in series to the sixth switching element, the seventh switching element and the eighth switching element may be connected in parallel, and the third circuit unit and the fourth circuit unit may be connected in series.

The control unit may control the first switching element, the third switching element, the seventh switching element, and the eighth switching element to always be in the on state.

When any one of the first switching element and the third switching element fails, the control unit may turn on the other one of the first switching element and the third switching element, turn on the second switching element, and turn off the fourth switching element in a first period, and may turn off the second switching element and turn on the fourth switching element in a second period.

When any one of the seventh switching element and the eighth switching element fails, the control unit may turn on the other one of the seventh switching element and the eighth switching element.

When the first switching element, the fourth switching element, and the fifth switching element are in an on state and the second switching element, the third switching element, and the sixth switching element are in an off state, a current may flow from the second load to the first load.

When the second switching element, the third switching element and the sixth switching element are in the on state and the first switching element, the fourth switching element and the fifth switching element are in the off state, a current may flow from the first load to the second load.

Advantageous Effects

According to a configuration of the present invention, a ladder bridge circuit capable of switching a direction of a current using a larger variety of paths than an H bridge circuit can be provided.

That is, since the ladder bridge circuit is a high voltage output circuit, switching elements constituting the H bridge circuit can fail. When any one of the switching elements fails, a complementary circuit is provided so that a current can flow through another path and the output circuit can be stably driven by controlling an on/off operation of the switching elements.

Further, some of the switching elements can be controlled to be in an on state so that a surge voltage can be dispersed over a plurality of paths and the probability of a failure of the switching elements can be reduced.

Further, when a ladder bridge circuit according to the present invention is used in a defibrillator, a high voltage can be switched in various directions so that the high voltage is not transmitted to a human body.

MODES OF THE INVENTION

Figure 1:
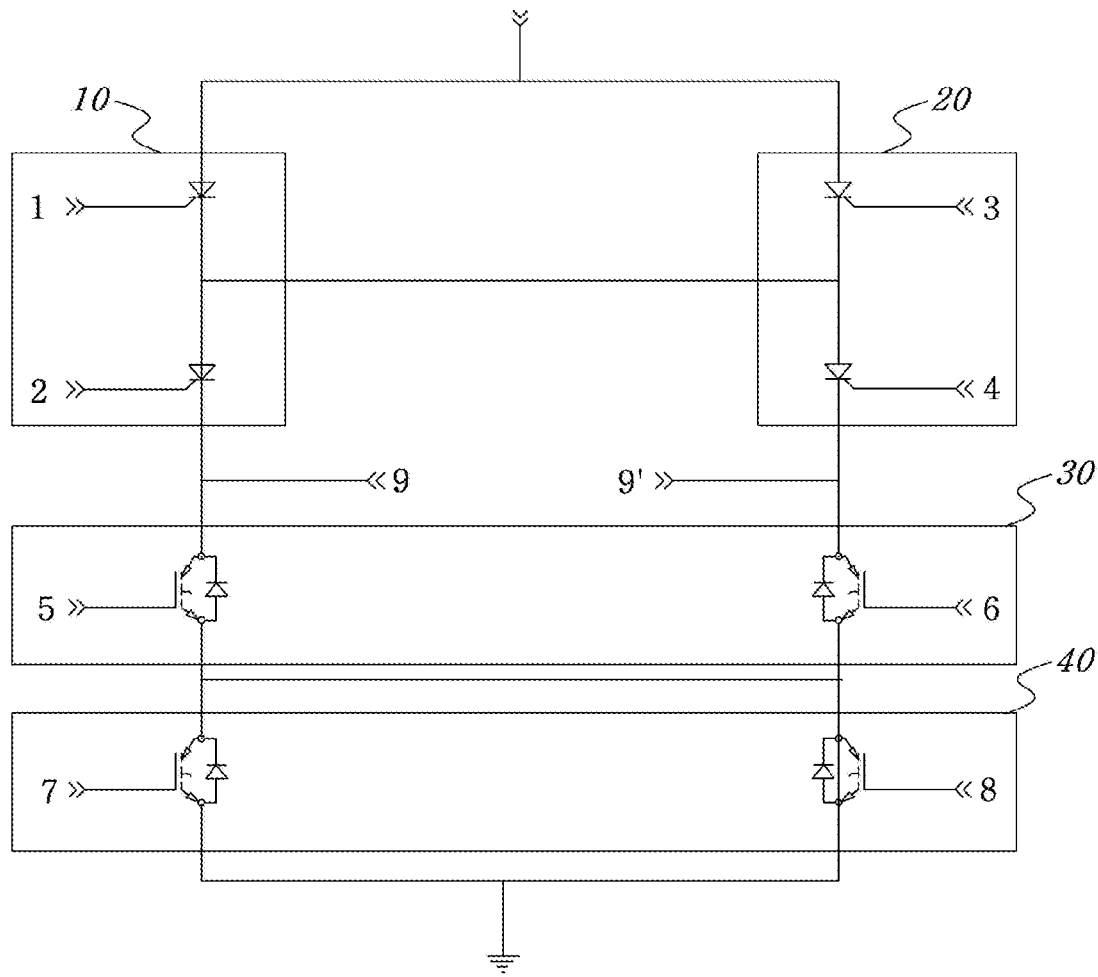
FIG. 1 is a circuit diagram illustrating an example of a ladder bridge circuit constituting a defibrillator according to an embodiment of the present invention.

Specific structural and functional descriptions of embodiments of the present invention disclosed in this specification or application are only for the purpose of describing embodiments of the present invention, and the embodiments of the present invention may be embodied in various forms and are not to be construed as limited to the embodiments described in this specification or application.

While the embodiments of the present invention may be modified in various ways and take on various alternative forms, specific embodiments thereof are shown in the drawings and described in detail in this specification or application. There is no intent to limit the present invention to the particular forms disclosed. On the contrary, the present invention is to cover all modifications, equivalents, and alternatives falling within the spirit and scope of the appended claims.

It should be understood that, although the terms "first," "second," and the like may be used herein to describe various elements, the elements are not limited by the terms. The terms are only used to distinguish one element from another element. For example, a first element could be termed a second element, and, similarly, a second element could be termed a first element, without departing from the scope of the present invention.

It should be understood that when an element is referred to as being "connected" or "coupled" to another element, the element may be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between," "adjacent" versus "directly adjacent," and the like).

The terminology used herein is for the purpose of describing particular embodiments only and is not intended to be limiting of the present invention. As used herein, the singular forms "a," "an," and "the" are intended to also include the plural forms, unless the context clearly indicates otherwise. It should be further understood that the terms "comprise," "comprising," "include," and/or "including," when used herein, specify the presence of stated features, integers, steps, operations, elements, parts, or combinations thereof, but do not preclude the presence or addition of one or more other features, integers, steps, operations, elements, parts, or combinations thereof.

Unless otherwise defined, all terms (including technical and scientific terms) used herein have the same meaning as commonly understood by one of ordinary skill in the art to which this invention belongs. It should be further understood that terms, such as those defined in commonly used dictionaries, should be interpreted as having a meaning that is consistent with their meaning in the context of the relevant art and are not to be interpreted in an idealized or overly formal sense unless expressly so defined herein.

Hereinafter, exemplary embodiments of the present invention will be described in detail with reference to the accompanying drawings. Like reference numerals in the drawings denote like elements.

Figure 2:
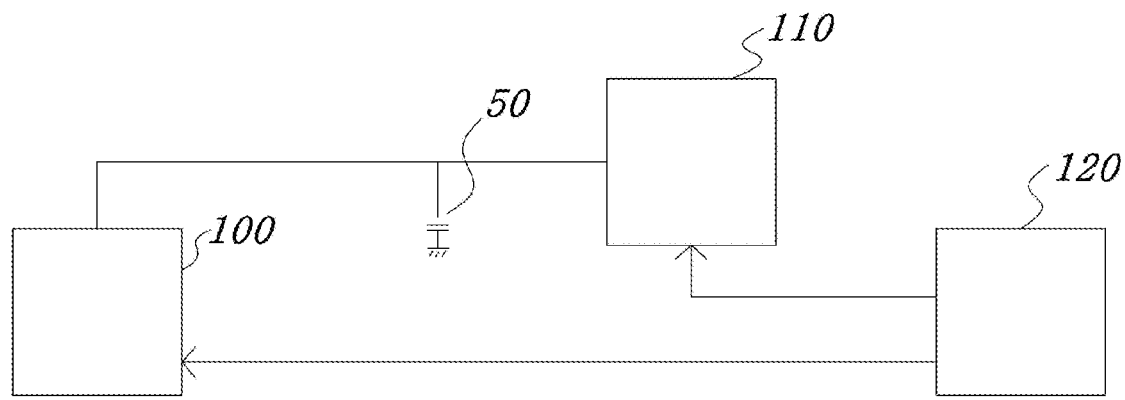
FIG. 2 is a block diagram of components constituting the defibrillator according to the embodiment of the present invention the defibrillator.

FIG. 1 is a circuit diagram illustrating an example of a ladder bridge circuit constituting a defibrillator according to an embodiment of the present invention, FIG. 2 is a block diagram of components constituting the defibrillator according to the embodiment of the present invention the defibrillator, and FIGS. 3A to 4B are views illustrating examples of a current flow of the ladder bridge circuit constituting the defibrillator according to the embodiment of the present invention.

Referring to FIGS. 1 and 2, a defibrillator 200 according to the embodiment of the present invention may include a high voltage capacitor 50, a ladder bridge circuit 100, a high voltage generator 110, and a control unit 120.

The high voltage capacitor 50 may be charged by a high voltage generated by the high voltage generator 110, and the control unit 120 may control an on/off operation of a plurality of switching elements 1 to 8 constituting the ladder bridge circuit 100 when a shock is required so that the high voltage charged in the high voltage capacitor 50 may be applied to a load between a first load 9 and a second load 9', for example, an electrode pad (not illustrated).

The ladder bridge circuit 100 may be connected to one end of the high voltage capacitor 50 and include a first circuit unit 10 including a first switching element 1 and a second switching element 2, a second circuit unit 20 including a third switching element 3 and a fourth switching element 4, a third circuit unit 30 including a fifth switching element 5 and a sixth switching element 6, and a fourth circuit unit 40 including a seventh switching element 7 and an eighth switching element 8.

Specifically, the first circuit unit 10 and the second circuit unit 20 are connected in parallel, the first switching element 1 and the second switching element 2 in the first circuit unit 10 are connected in series, and the third switching element 3 and the fourth switching element 4 in the second circuit unit 20 are connected in series.

The high voltage capacitor 50 is connected to one end of each of the first switching element 1 and the third switching element 3, and one end of each of the second switching element 2 and the fourth switching element 4 is connected in series to corresponding one of the other ends of the first switching element 1 and the third switching element 3.

The first load 9 may be connected between the second switching element 2 and the fifth switching element 5, and the second load 9' may be connected between the fourth switching element 4 and the sixth switching element 6. An electrode pad (not illustrated) to be attached to a human body may be connected to the first load 9 and the second load 9'. That is, when the electrode pad is connected between the first load 9 and the second load 9' as a load, the first load 9 and the second load 9' may be electrically connected.

One end of each of the first circuit unit 10 and the second circuit unit 20 is connected to the high voltage capacitor 50, and the other end of each of the first circuit unit 10 and the second circuit unit 20 is connected to one end of the third circuit unit 30. Specifically, the other end of the first circuit unit 10 is the other end of the second switching element 2 and is connected to one end of the fifth switching element 5, and the other end of the second circuit unit 20 is the other end of the fourth switching element 4 and is connected to one end of the sixth switching element 6.

The other end of the third circuit unit 30 is connected to one end of the fourth circuit unit 40, specifically, the other end of the fifth switching element 5 is connected in series to one end of the seventh switching element 7 of the fourth circuit unit 40, and the other end of the sixth switching element 6 is connected in series to one end of the eighth switching element 8 of the fourth circuit unit 40. The one end of the fourth circuit unit 40 is the one end of the seventh switching element 7 and the one end of the eighth switching element 8. Here, the seventh switching element 7 and the eighth switching element 8 are connected in parallel, and the third circuit unit 30 and the fourth circuit unit 40 are connected in series.

The control unit 120 may determine whether the first switching element 1, the third switching element 3, the seventh switching element 7, and the eighth switching element 8 are faulty, and may control only a non-failed switching element among the first switching element 1 and the third switching element 3 to be in an on state and only a non-failed switching element among the seventh switching element 7 and the eighth switching element 8 to be in the on state according to a result of the determination.

Further, the control unit 120 may control the first switching element 1 and the third switching element 3, the seventh switching element 7, and the eighth switching element 8 to always be in the on state when all of the switching elements normally operate.

In this case, the control unit 120 may control only one of the second switching element 2 and the fourth switching element 4 to be in the on state in a first phase, and may control only the other one thereof to be in the on state in a second phase. Further, the control unit 120 may turn on the sixth switching element 6 when the second switching element 2 is in the on state, and may turn on the fifth switching element 5 when the fourth switching element 4 is in the on state.

Since the first switching element 1 and the third switching element 3 are always in the on state when a current is input from the high voltage capacitor 50 to the ladder bridge circuit 100, the current may be dispersed. Therefore, a surge voltage that may occur when power supply is suddenly turned on may be lowered, and thus a failure of a switching element may be prevented.

Figure 3A:
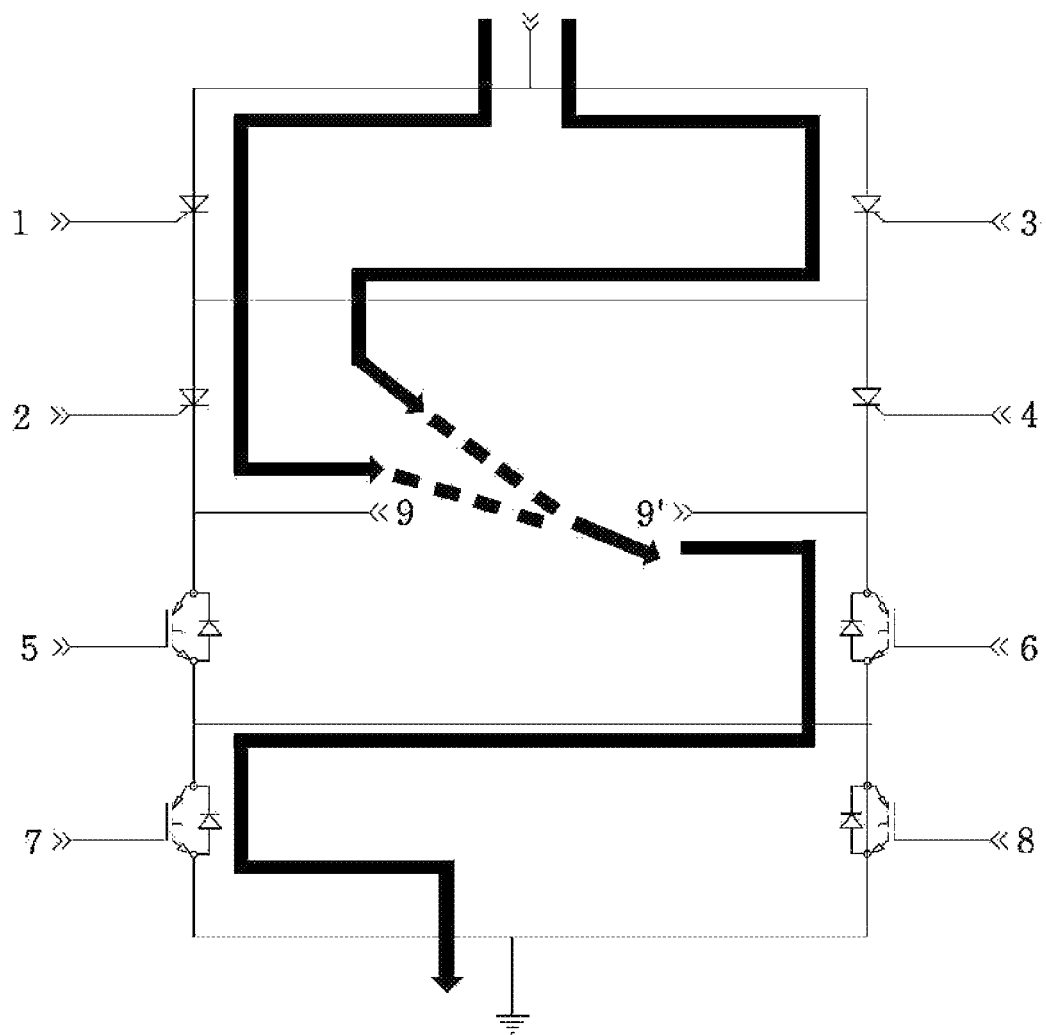
FIGS. 3A to 4B are views illustrating examples of a current flow of the ladder bridge circuit constituting the defibrillator according to the embodiment of the present invention.

Referring to FIG. 3A, a current flow in the first phase according to an embodiment of the present invention is illustrated. That is, both a first path and a second path in the first phase are formed. In the first phase, both the first switching element 1 and the third switching element 3 are in the on state, and thus a current input from the high voltage capacitor 50 passes through both the first switching element 1 and the third switching element 3. However, the current passing through the first switching element 1 also passes through the second switching element 2, and the current passing through the third switching element 3 also passes through the second switching element 2.

That is, since the third switching element 3 is turned on even in the first phase, a failure of the first switching element 1 due to a surge voltage that may occur when the current input from the high voltage capacitor 50 passes through only the first switching element 1 may be prevented.

Figure 3B:
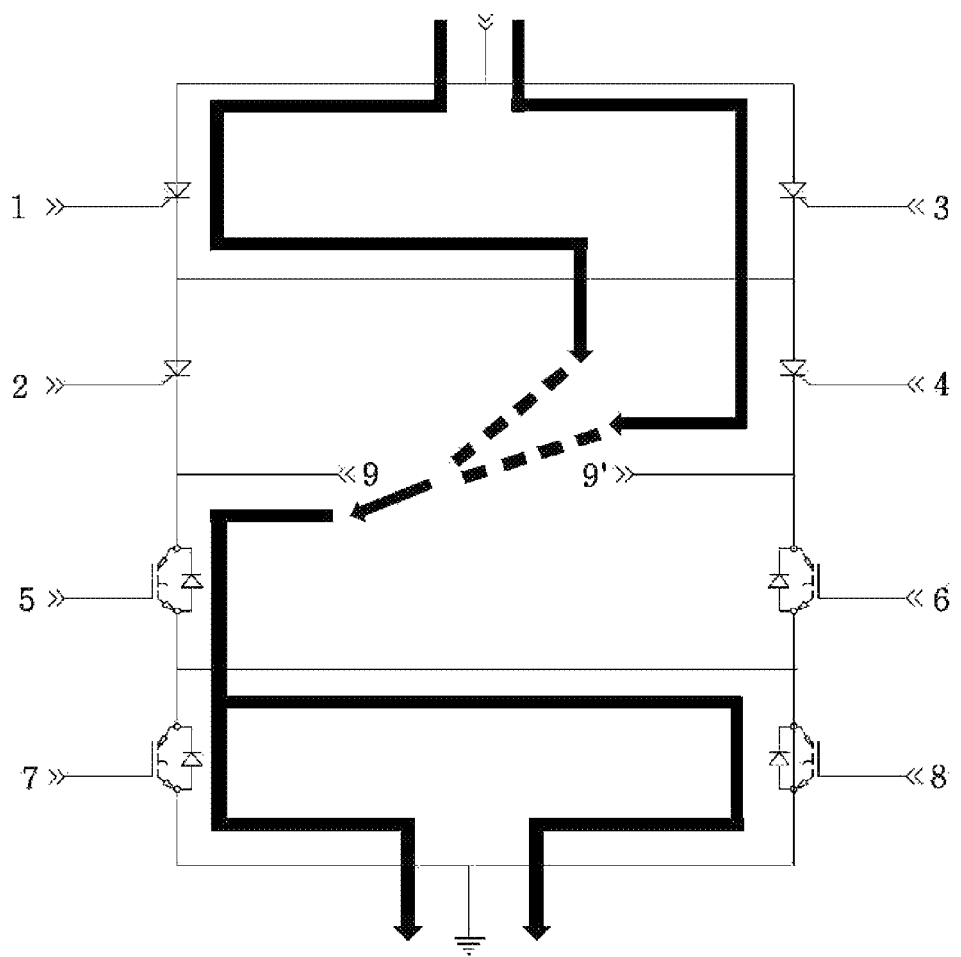

Referring to FIG. 3B, a current flow in the second phase according to an embodiment of the present invention is illustrated. In the second phase, both the first switching element 1 and the third switching element 3 are in the on state, and thus the current input from the high voltage capacitor 50 passes through both the first switching element 1 and the third switching element 3. However, the current passing through the first switching element 1 also passes through the fourth switching element 4, and the current passing through the third switching element 3 also passes through the fourth switching element 4.

That is, since the first switching element 1 is turned on even in the second phase, a failure of the third switching element due to a surge voltage that may occur when the current input from the high voltage capacitor 50 passes through only the third switching element 3 may be prevented.

Figure 4A:
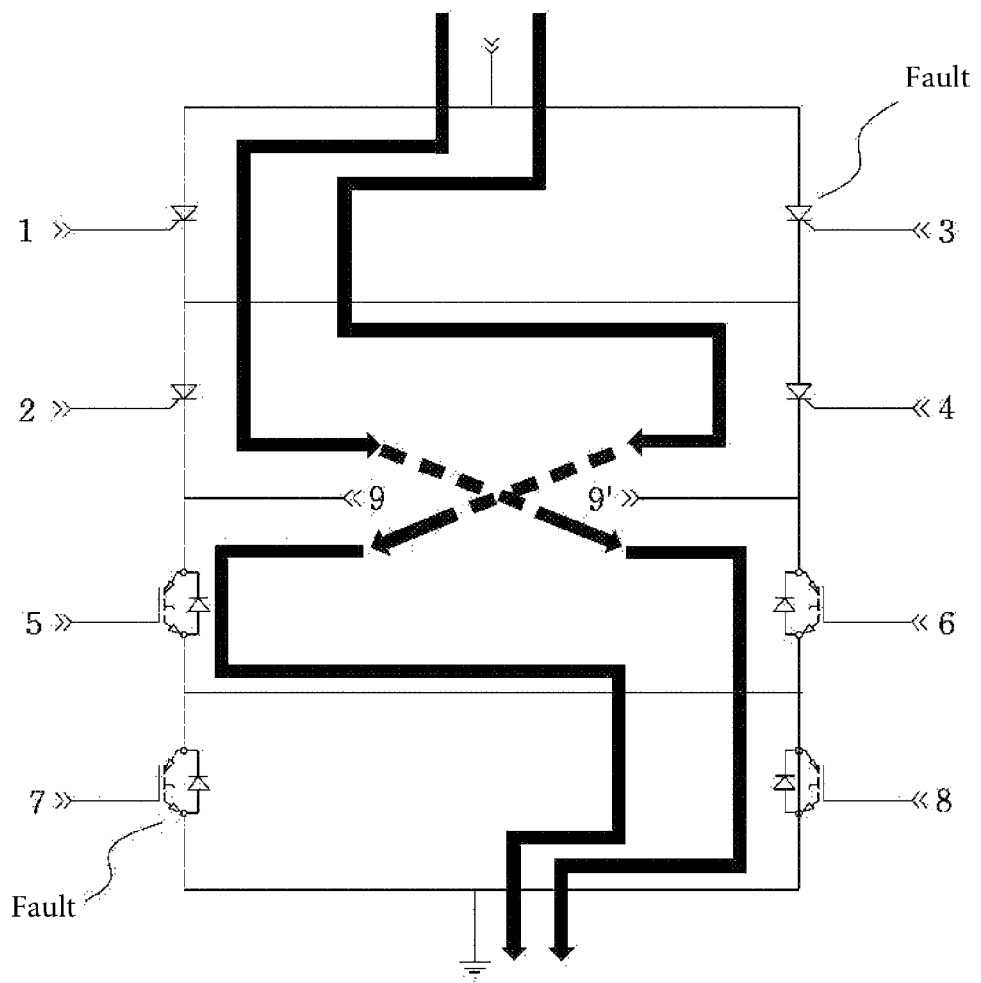
Figure 4B:
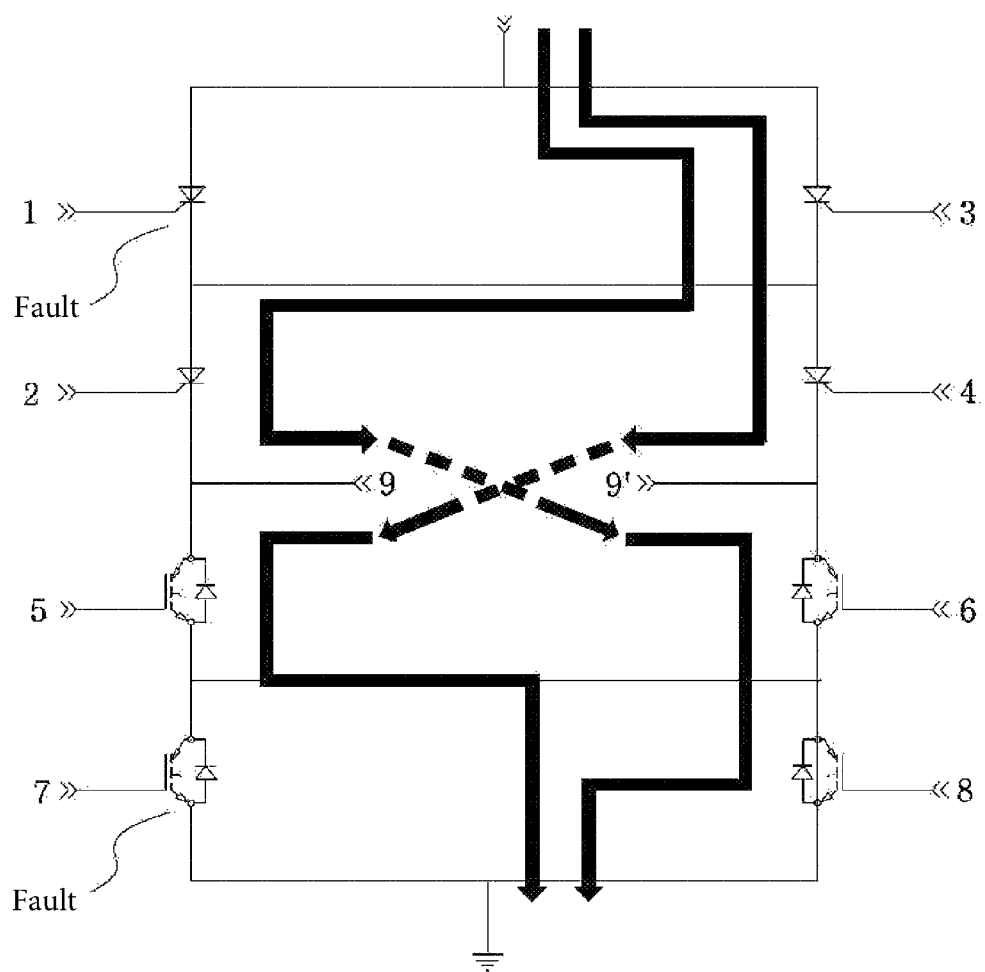

FIG. 4A is a view illustrating current flows in the first phase and the second phase when the third switching element 3 and the seventh switching element 7 fail, and FIG. 4B is a view illustrating current flows in the first phase and the second phase when the first switching element 1 and the seventh switching element 7 fail.

Referring to FIG. 4A, when the control unit 120 determines that the third switching element 3 and the seventh switching element 7 fail, the control unit 120 may control the on/off states of the switching elements so that the current path in the first phase becomes a path 501 having an order of the first switching element 1, the second switching element 2, the first load 9, the second load 9', the sixth switching element 6, and the eighth switching element 8.

Further, the control unit 120 may control the on/off states of the switching elements so that the current path in the second phase becomes a path 502 having an order of the first switching element 1, the fourth switching element 4, the second load 9', the first load 9, the fifth switching element 5, and the eighth switching element 8.

Referring to FIG. 4B, when the control unit 120 determines that the first switching element 1 and the seventh switching element 7 fail, the control unit 120 may control the on/off states of the switching elements so that the current path in the first phase becomes a path having an order of the third switching element 3, the second switching element 2, the first load 9, the second load 9', the sixth switching element 6, and the eighth switching element 8.

Further, the control unit 120 may control the on/off states of the switching elements so that the current path in the second phase becomes a path having an order of the third switching element 3, the fourth switching element 4, the second load 9', the first load 9, the fifth switching element 5, and the eighth switching element 8.

Further, when the control unit 120 determines that the first switching element 1 and the eighth switching element 8 fail, the control unit 120 may control the on/off states of the switching elements so that the current path in the first phase becomes a path having an order of the third switching element 3, the second switching element 2, the first load 9, the second load 9', the sixth switching element 6, and the seventh switching element 7.

Further, the control unit 120 may control the on/off states of the switching elements so that the current path in the second phase becomes a path having an order of the third switching element 3, the fourth switching element 4, the second load 9', the first load 9, the fifth switching element 5, and the seventh switching element 7.

That is, even when one of the first switching element 1 and the third switching element 3 and one of the seventh switching element 7 and the eighth switching element 8 fail, both the current path in the first phase and the current path in the second phase are formed, and thus reliability of the defibrillator may be secured.

Here, the switching elements means elements for switching high currents and high voltages and may include a silicon controlled rectifier (SCR), an insulated-gate bipolar transistor (IGBT), a bipolar and metal-oxide-semiconductor field-effect transistor (BIMOSFET), and the like. The high voltage generator 110 may include a transformer, a snubber circuit, and the like, which are connected to a battery to receive power and are operated by receiving a pulse-width modulation (PWM) control signal from the control unit 120. The control unit 120 may include a plurality of processors, such as a monitoring processor, a sub processor, a main processor, and the like, and the sub processor and the monitoring processor may communicate with the main processor through universal asynchronous receiver-transmitter (UART) communication. The monitoring processor may monitor states of a battery, a button, and a light-emitting diode (LED) and transmit the states to the main processor, and the sub processor may receive a signal from the monitoring processor through the main processor and control a PWM signal of the high voltage generator 110 and the on/off states of the switching elements of the ladder bridge circuit 100.

In an embodiment, the case in which the first switching element 1, the second switching element 2, the third switching element 3, and the fourth switching element 4 are SCRs and the fifth switching element 5, the sixth switching element 6, the seventh switching element 7, and the eighth switching element 8 are metal-oxide-semiconductor field-effect transistors (MOSFETs) is illustrated in the drawings, but the present invention is not limited thereto.

While the present invention has been particularly described with reference to exemplary embodiments, it should be understood by those of skilled in the art that various changes in form and details may be made thereto without departing from the spirit and scope of the present invention. Therefore, the exemplary embodiments should be considered in a descriptive sense only and not for purposes of limitation. The scope of the present invention is defined not by the detailed description of the present invention but by the appended claims, and encompasses all modifications and equivalents that fall within the scope of the appended claims.

INDUSTRIAL APPLICABILITY

The present invention is a technique applied to a defibrillator field and is highly industrially applicable.

The invention claimed is:

1. A defibrillator providing a defibrillation shock including a defibrillation pulse forming a biphasic wave having a first phase and a second phase having polarity opposite that of the first phase, the defibrillator comprising:
a high voltage capacitor charged through a battery power source;
a ladder bridge circuit connected to one end of the high voltage capacitor; and
a control unit configured to control on/off states of at least one of a first switching element to an eighth switching element constituting the ladder bridge circuit,
wherein the ladder bridge circuit includes a first circuit unit and a second circuit unit having one ends connected to one end of the high voltage capacitor and connected in parallel, and a third circuit unit connected in series to the other ends of the first circuit unit and the second circuit unit,
the first circuit unit includes the first switching element having one end connected to the high voltage capacitor and the second switching element connected in series to the other end of the first switching element,
the second circuit unit includes the third switching element having one end connected to the high voltage capacitor and the fourth switching element connected in series to the other end of the third switching element,
the third circuit unit includes the fifth switching element and the sixth switching element connected in parallel and having one ends connected to the other ends of the first circuit unit and the second circuit unit,
the control unit controls only one of the second switching element and the fourth switching element to be in an on state in a first phase, and controls only the other one thereof to be in an on state in a second phase, and
the control unit turns on the sixth switching element when the second switching element is in the on state, and turns on the fifth switching element when the fourth switching element is in the on state.

2. The defibrillator of claim 1, wherein:
the ladder bridge circuit further includes a first load connected between the second switching element and the fifth switching element and a second load connected between the fourth switching element and the sixth switching element; and
the first load and the second load are electrically connected when a load is connected thereto.

* * * * *